United States Patent [19]

Gallaher et al.

[11] Patent Number: 5,585,366
[45] Date of Patent: Dec. 17, 1996

[54] LOWERING BLOOD CHOLESTEROL LEVELS USING WATER SOLUBLE CELLULOSE ETHERS

[75] Inventors: Daniel D. Gallaher, Roseville; Craig A. Hassel, Coon Rapids, both of Minn.

[73] Assignee: Regents of the University of Minnesota, Minneapolis, Minn.

[21] Appl. No.: 445,407

[22] Filed: May 19, 1995

Related U.S. Application Data

[60] Division of Ser. No. 840,178, Feb. 24, 1992, and a continuation-in-part of Ser. No. 666,392, Mar. 8, 1991, abandoned.

[51] Int. Cl.⁶ .......................... A01N 43/04; A01N 25/00; C07J 17/00; A23G 9/00
[52] U.S. Cl. .................. 514/57; 514/53; 514/54; 514/23; 514/181; 514/777; 536/56; 536/30; 536/114; 536/123.1; 536/123.13; 424/439; 426/567; 426/103
[58] Field of Search .................................. 514/57, 53, 54, 514/23, 781, 777; 424/9.35, 9.43, 439; 536/56, 30, 114, 123.13; 426/567, 103

[56] References Cited

U.S. PATENT DOCUMENTS

| | | | |
|---|---|---|---|
| 2,701,782 | 2/1955 | Culter et al. | 167/56 |
| 2,802,741 | 8/1957 | Weaver et al. | 99/94 |

(List continued on next page.)

FOREIGN PATENT DOCUMENTS

| | | | |
|---|---|---|---|
| 0005977 | 12/1979 | European Pat. Off. | A21D 2/18 |
| 0278464 | 8/1988 | European Pat. Off. | A61K 91/16 |
| 0309029 | 3/1989 | European Pat. Off. | A21D 2/36 |
| 0323666 | 7/1989 | European Pat. Off. | A61K 31/785 |
| 0362926 | 4/1990 | European Pat. Off. | A61K 35/78 |
| 58-135805 | 8/1983 | Japan | A61K 9/14 |
| 60-142911 | 7/1985 | Japan | A61K 7/16 |
| 62-122671 | 6/1987 | Japan | A61K 31/00 |
| 62-266056 | 11/1987 | Japan | A61F 9/00 |
| 232433 | 12/1990 | New Zealand | A23L 1/24 |
| 2021948 | 12/1979 | United Kingdom | A61K 9/14 |
| 2097804 | 11/1982 | United Kingdom | C08L 1/00 |
| WO92/15312 | 9/1992 | WIPO | A61K 31/715 |

OTHER PUBLICATIONS

Allain, et al., *Clin. Chem.*, 20, 470 (1974).
Anderson, et al., "Dietary Fiber: Hyperlipidemia, Hypertension, and Coronary Heart Disease," *Am. J. Gastroenterology*, 81, (1986).
Anderson, et al., "Dietary Fiber and Coronary Heart Disease," *Food Science and Nutrition*, 29, (1990).
Anderson, J. W., et al., "Oat–Bran Cereal Lowers Serum Total and LDL Cholesterol in Hypercholesterolemic Men," *Am. J. Clin. Nut.*, 52, 495–499 (1990).
Anderson, J. W., et al., "Cholesterol–Lowering Effects of Psyllium Hydrophilic Mucilloid for Hyper cholesterolemic Men," *Arch. Intern. Med.*, 148, 292–296 (1988).
Anderson, J. W., et al., "Hypercholesterolemic Effects of Oat–Bran of Bean Intake for Hypercholesterolemic Men," *Am. J. Clin. Nut.*, 40, 1146–1150 (1984).
Arutyunova, M. B., et al., "Influence of Rations Containing Food Fibers on the Levels of General Lipids and Cholesterol in the blood and Liver of Rats Under the Conditions of a 6.5 Month Experiment," *Vopr. Pitan.*, (Russ), Issue 6, pp. 47–50 (1989), *Chemical Abstracts*, 112(15), 138045f, (Abstract in English).

(List continued on next page.)

*Primary Examiner*—John Kight
*Assistant Examiner*—Louis N. Leary
*Attorney, Agent, or Firm*—Schwegman, Lundberg, Woessner & Kluth, P.A.

[57] ABSTRACT

A method for reducing the cholesterol level in mammalian blood by administering a water soluble cellulose ether thereto. The cellulose ethers have a viscosity, measured as a 2% aqueous solution at 20° C., of at least about 35 cps. Oral administration is preferred, and, in one embodiment the high viscosity water soluble cellulose ether is hydroxypropyl methylcellulose, contained in a nutritious foodstuff.

3 Claims, 2 Drawing Sheets

U.S. PATENT DOCUMENTS

| | | | |
|---|---|---|---|
| 2,831,852 | 4/1958 | Savage | 424/9.35 |
| 2,883,327 | 4/1959 | Dale et al. | 167/82 |
| 3,308,020 | 3/1967 | Wolf et al. | 167/65 |
| 3,342,805 | 9/1967 | Callihan et al. | 260/232 |
| 3,383,281 | 5/1968 | Wolf et al. | 167/65 |
| 3,388,082 | 6/1968 | Rogers et al. | 260/17 |
| 3,499,960 | 3/1970 | Macek et al. | 424/33 |
| 3,627,872 | 12/1971 | Parkinson | 424/79 |
| 3,709,876 | 1/1973 | Glomski et al. | 260/231 A |
| 3,721,735 | 3/1973 | Thifflault | 424/195 |
| 4,005,195 | 1/1977 | Jandacek | 424/439 |
| 4,109,018 | 8/1978 | Thompson | 426/62 |
| 4,175,124 | 11/1980 | Hyldon | 424/439 |
| 4,232,007 | 11/1979 | Kajharaetal | 424/439 |
| 4,251,519 | 2/1981 | Robbins | 424/439 |
| 4,265,879 | 5/1981 | Fields | 424/439 |
| 4,284,649 | 8/1981 | Wiczer | 424/362 |
| 4,326,523 | 4/1982 | Wolfrom | 424/439 |
| 4,362,711 | 12/1982 | Cerami | 424/439 |
| 4,389,393 | 6/1983 | Schor et al. | 424/9.35 |
| 4,410,693 | 11/1983 | Gibson | 536/56 |
| 4,432,968 | 2/1984 | Page | 424/439 |
| 4,451,490 | 5/1984 | Silverman et al. | 426/553 |
| 4,461,782 | 7/1984 | Robbins et al. | 426/549 |
| 4,477,657 | 11/1984 | Strange et al. | 536/91 |
| 4,520,017 | 5/1985 | Tunc | 514/54 |
| 4,614,545 | 9/1986 | Hess | 424/439 |
| 4,626,287 | 12/1986 | Shah | 514/54 |
| 4,704,285 | 11/1987 | Alderman | 424/9.35 |
| 4,729,895 | 3/1988 | Makino | 424/439 |
| 4,732,917 | 3/1988 | Shah | 514/54 |
| 4,734,285 | 3/1988 | Alderman | 424/439 |
| 4,754,027 | 6/1988 | Applegrin | 536/114 |
| 4,789,664 | 12/1988 | Seligson | 514/23 |
| 4,820,813 | 4/1989 | Schulz | 536/84 |
| 4,824,675 | 4/1989 | Wong et al. | 424/438 |
| 4,846,889 | 7/1989 | Meyer | 514/23 |
| 4,849,222 | 7/1989 | Broaddus | 424/439 |
| 4,849,227 | 7/1989 | Cho | 424/439 |
| 4,883,788 | 11/1989 | Day | 514/57 |
| 4,892,747 | 1/1990 | Ohta | 426/618 |
| 4,895,723 | 1/1990 | Amer et al. | 424/79 |
| 4,900,573 | 2/1990 | Meyers | 426/302 |
| 4,915,954 | 4/1990 | Ayer et al. | 424/473 |
| 4,919,938 | 4/1990 | Lovegrove et al. | 424/480 |
| 4,923,981 | 5/1990 | Weibel | 536/56 |
| 4,950,140 | 8/1990 | Pflaumer | 424/439 |
| 4,959,466 | 9/1990 | White | 514/57 |
| 4,996,063 | 2/1991 | Ingelett | 426/21 |
| 5,130,333 | 7/1992 | Pan | 514/57 |
| 5,213,829 | 5/1993 | Cox et al. | 424/9.35 |
| 5,219,599 | 6/1993 | Cox et al. | 424/9.35 |
| 5,268,181 | 12/1993 | O'Neill et al. | 424/9.35 |
| 5,281,584 | 1/1994 | Toberg | 514/57 |

OTHER PUBLICATIONS

Benko, S., et al., "Effect of Cholesterol feeding and Methyl Cellulose Administration on the total Lipid and Total Cholesterol Content in the Serum and Tissues," *Chem. Abstracts,* 72, p. 236, Abstract No. 109611n, (1970).

Benko, et al., *Corvasa,* 12, 65 (1970).

Bosello, O., et al., "Effects of guar gum on Plasma Lipoproteins and Apolipoproteins C–II and C–III in Patients Affected by Familial Combined Hyperlipoproteinemia," *Am. J. Clin Nut.,* 40, 1165–1174 (1984).

Butler, R. W., et al., "Hydroxypropylcellulose," In: *Handbook of Water–Soluble Gums and Resins,* Davidson, R. L., (ed.), McGraw–Hill Book Company, N.Y., pp. 13–1—13–17 (1980).

Chen, W.–J. L., et al., "Effects of Plant Fiber in Decreasing Plasma Total Cholesterol and Increasing High–Density Lipoprotein Cholesterol (40671)," *Proc. Soc. Exp. Biol. Med.,* 162, 310–313 (1979).

Costa, M. A., et al., "Effects of Dietary Cellulose, Psyllium Husk and Cholesterol on Fecal and Colonic Microbial Metabolism in Monkeys," *J. Nutr.,* 119, 986–992 (1989).

Fuse, K., et al., "Effects of Pectin on Fatty Acid and Glucose Absorption and on Thickness of Unstirred Water Layer on Rat and Human Intestine," *Digest. Dis. Sci.,* 34, 1109–1116 (1989).

Gallaher et al., *Nutr. Res.,* 10, 1311–1323 (1990).

Gold, K. V., et al., "Oat Bran as a Cholesterol–Reducing Dietary Adjunct in a Young, Healthy Population," *West. J. Med.,* 148, 299–302 (1988).

Greminger, G. K., et al, "Alkyl and Hydroxyalkylalkylcellulose," In: *Handbook of Water–Soluble Gums and Resins,* Davidson, R. L., (ed.), McGraw–Hill Book Company, NY., pp. 3–1—3–25 (1980).

Hillman, L. C., et al., "The Effects of the Fiber Components Pectin, cellulose and Lignin on Serum Cholesterol Levels," *Am. J. Clin. Nutr.,* 42, 207–213 (1985).

Holt, S., et al., "Effect of Gel Fibre on Gastric Emptying and Absorbtion of Glucose and Paracetamol," *The Lancet,* 636–639 (Mar., 1979).

Jenkins, D. J. A., et al., "Dietary Fibres, Fibre Analgoues, and glucose Tolerance: Importance of Viscosity," *Brit. Med. J.,* 1, 1392–1394 (1978).

Kirk–Othmer Concise Encyclopedia of Chemical Technology, pp. 231–232, M. Grayson (ed.), Wiley–Interscience, New York, NY (1985).

Kritchedsky et al., "Influence of Dietary Fiber on Cholesterol Metabolism in Experimental Animals," *CRC Handbook of Dietary Fiber in Human Nutrition,* pp. 129–142 (1986).

Lalor, B. C., et al., "Placebo–Controlled Trial of the Effects of Guar Gum and Metaformin on Fasting Blood Glucose and Serum Lipids in Obese, Type 2 Diabetic Patients," *Diabetic Med.,* 7, 242–245 (1990).

Larosa et al., "The Cholesterol Facts . . . ," *Circulation,* 81, 1721–1733 (1990).

Lo, G. S., et al. "Soy Cotyledon Fiber Products Reduce Plasma Lipids," *Atherosclerosis,* 82, 59–67 (1990).

Martindale—The Extra Pharmacopoeia, 28th ed., Renolds, J. E. F., (ed.), The Pharmaceutical Press, London, pp. 947–963 (1982).

McIvor, M. E., et al., "Flattening Postprandial Blood Glucose Responses with Guar Gum: Acute Effects," *Diabetes Care,* 8, 274–278 (1985).

Morgan, L. M., et al., "The Effect of Soluble–and Insoluble–Fiber Supplementation on Post–Prandial Glucose Tolerance, Insulin and Gastric Inhibitory Polypeptide Secretion in Healthy Subjects," *Brit. J. Nutr.,* 64, 103–110 (1990).

Munoz et al., *Am. J. Clin. Nutr.,* 32, 580 (1979).

Nightindale, *Diss. Abstracts Int.,* 49, 3879b (1989).

Nightingale, *Chem. Abstracts,* 110, Abstract No. 205436h (1989).

Nightingale, J. A. S., "Lipid Binding From Aqueous Solution by Lipid Conjugated Hydroxypropylmethylcellulose," Ph.D. Thesis, University of Washington, (1988).

Noller, *Chemistry of Organic Compounds,* (2nd ed.). pp. 404–405, W. B. Sanders Co., London, England (1957).

Powell, G. M., "Hydroxymethylcellulose," In: *Handbook of Water–Soluble Gums and Resins*, Davidson, R. L., (ed.), McGraw–Hill Book Company, NY., pp. 12–1—12–22 (1980).

Reppas, C, et al., "Effect of Hyproxypropylmethycellulose on Gastrointestinal Transit and Luminal Viscosity in Dogs," *Gastroenterology*, 100, 1217–1223 (1991).

Requejo, F., et al., "Effects of α–Glucosidase Inhibition and Viscous Fibre on Diabetic Control and Postprandial Gut Hormone Responses," *Diabetic Med.*, 7, 515–520 (1990).

Schwartz, S. E., et al., "Sustained Pectin Ingestion: Effect on Gastric Emptying and Glucose Tolerance in Non–Insulin–Dependent Diabetic Patients," *Am. J. Clin. Nutr.*, 48, 1413–1417 (1988).

Seidner, D. L, et al. "Esophageal Obstruction After Ingestion of a Fibre–containing diet Pill," *Gastroenterology*, 99, 1820–1822 (1990).

Sirois et al., "Gastric Emptying of Nondigestible Solids in Dogs: A Hydrodynamic Correlation," *Am. J. Physiol.*, 258, G65–G72 (1990).

Stahl, M., et al., *Schweiz. Med. Wschr.*, 120, 402–408 (1990).

Suji, et al., "Effects of Polysaccharides on Cholesterol Metabolism, VII. Effects of Various Synthetic Polymers on Serum and Liver Cholesterol Levels in Rats," *Chemical Abstracts*, 89(7), p. 485, Abstract No. 58752a (Aug. 1978) (*Eiyogaku Zasshi*, 35(5), 227–234 (1977)).

Superko et al., *Am. J. Cardiol.*, 65, 51 (1988).

Swain, J. F., et al., "Comparison of the Effects of Oat Bran and Low–Fiber Wheat on Serum Lipoprotein Levels and Blood Pressure," *New Eng. J. Med.*, 322, 147–152 (1990).

*The United States Pharmacopeia: The National Formulary*, Published by United States Pharmacopeial Convention, Inc., pp. 670–671, 865 (1990).

Topping et al., *Brit. J. Nutr.*, 59, 21 (1988).

Torsdottir, I., et al., "Dietary Guar Gum Effects on Postprandial Blood Glucose, Insulin and Hydroxyproline in Humans," *J. Nutr.*, 119, 1925–1931 (1989).

Tsai, A. C., et al., "Effects of Soy Polysaccharide in Postprandial Plasma glucose, Insulin, Glucagon, Pancreatic Polypeptide, Somatostatin, and Triglyceride in Obese Diabetic Patients," *Am. J. Clin. Nutr.*, 45, 596–601 (1987).

Tsuji, *Chem. Abstracts*, 89, 58752aa (1978).

Uusitupa, M., et al., "Metabolic and Nutritional Effects of Long–Term Use of Guar Gum in the Treatment of Noninsulin–Dependent Diabetes of Poor Metabolic Control," *Am. J. Clin. Nutr.*, 49, 345–351 (1989).

Warnick et al., *Clin. Chem.*, 28, 1379 (1982).

Yusef et al., "Overview of Results of Randomized Clinical Trials in Heart Disease," *JAMA*, 260, 2259–2263 (1988).

"Dietary Fiber and Health," A Council Report by the Council on Scientific Affairs Appearing in JAMA, vol. 262(4), (Jul. 28, 1989).

"National Education Programs Working Group Report on the Management of Patients with Hypertension and High Blood Cholesterol," *Ann. Intern. Med.*, 114, 224–237 (1990).

"Procter & Gamble's Metamucil Psyllium Cholesterol–Lowering Claim," *F–D–C Reports*, pp. 3–4 (Jul. 30, 1990).

LOWERING BLOOD CHOLESTEROL LEVELS USING WATER SOLUBLE CELLULOSE ETHERS

CROSS-REFERENCE TO RELATED APPLICATION

This is a division of copending application Ser. No. 07/840,178, filed Feb. 24, 1992. This application is a continuation-in-part of U.S. patent application Ser. No. 07/666,392 filed Mar. 8, 1991, now abandoned.

FIELD OF THE INVENTION

The present invention relates to methods and foodstuffs useful in reducing total plasma cholesterol levels in mammals, and specifically to methods of using water soluble cellulose ethers to reduce cholesterol levels.

BACKGROUND OF THE INVENTION

Elevated total plasm cholesterol (TPC) levels, also referred to as serum cholesterol levels, are firmly established as a significant factor in the development of coronary heart disease. Consequently, there is a considerable interest in discovering and developing methods for reducing TPC levels. Although drugs are now available that can produce significant reductions in serum cholesterol, most if not all have undesirable side effects.

A number of studies have been conducted on the role of dietary fiber in health and disease. Studies comparing the effects of various fiber sources on cholesterol concluded that different fiber sources affect TPC levels in mammals differently. According to these studies, fibers such as cellulose are not hypocholesterolemic in mammals. See *CRC Handbook of Dietary Fiber in Human Nutrition*, "Influence Of Dietary Fiber On Cholesterol Metabolism In Experimental Animals," by D. Kritchevsky and J. A. Story et al., Chapter 4.3 (1986 G. Spiller, Ed.).

With respect to cellulose derivatives, D. L. Topping, et al., *J. Nutr.*, 59, 21 (1988) tested the cholesterol-lowering effect of methylcellulose of low, medium and high viscosity (25–1500 cps at 2% solution) in rats. They documented changes in carbohydrate and fatty acid metabolism and speculated that those changes are due to the slowed digestion and absorption of nutrients in the small intestine. However, plasma and liver cholesterol concentrations were not altered by these materials.

Therefore, a continuing need exists for agents capable of reducing plasma cholesterol levels.

SUMMARY OF THE INVENTION

The present invention provides a therapeutic method to lower the levels of total plasma cholesterol (TPC) in mammalian, i.e. human, blood, which can be significantly reduced by administering to the mammal an effective amount of a water soluble cellulose ether. A wide variety of cellulose ethers effective in the practice of the present method are commercially available, or can be readily obtained via conventional organic synthetic methodology. These materials are nontoxic, at the dosages administered, and are generally tasteless and essentially non-caloric.

Although cellulose ethers have been used in a variety of foodstuffs to improve certain functional properties, such as emulsification, texture or moisture retention, the amounts used are usually less than 0.5% of the foodstuff. These levels are too low to have any significant physiological effect, such as the cholesterol lowering effect which is the basis of the present invention.

Therefore, the present invention also provides processed foodstuffs intended for human ingestion which comprise an amount of one or more water soluble cellulose ethers in an amount effective to lower TPC upon ingestion of an amount of the foodstuff, alone, or in combination with other foods used to meet the daily caloric requirements of the subject. In contrast to the small amounts conventionally employed in processed foodstuffs, the foodstuffs which are the subject of the present invention will preferably comprise about 2–20 wt-% of one or more water soluble cellulose ethers, preferably about 5–15 wt-% of cellulose ether(s). At these levels, about 1–30 g, preferably about 2–10 g, of cellulose ether will be ingested daily by the mammal, e.g., by a human, per 1000 kilocalories of total food consumed daily. Therefore, to achieve a useful cholesterol-lowering effect ($\geq 5-10\%$) in accord with the present method, an adult man would ingest about 2.5–10 g/day, preferably about 4–8 g/day, and an adult woman would ingest about 2–8 g/day, preferably about 3–7.5 g/day of a cellulose ether, such as a medium to high viscosity hydroxypropyl methyl cellulose. However, dosages as high as 30–35 g/day may be indicated for some human patients with highly elevated TPC.

DESCRIPTION OF THE PREFERRED EMBODIMENTS

Figure 1:
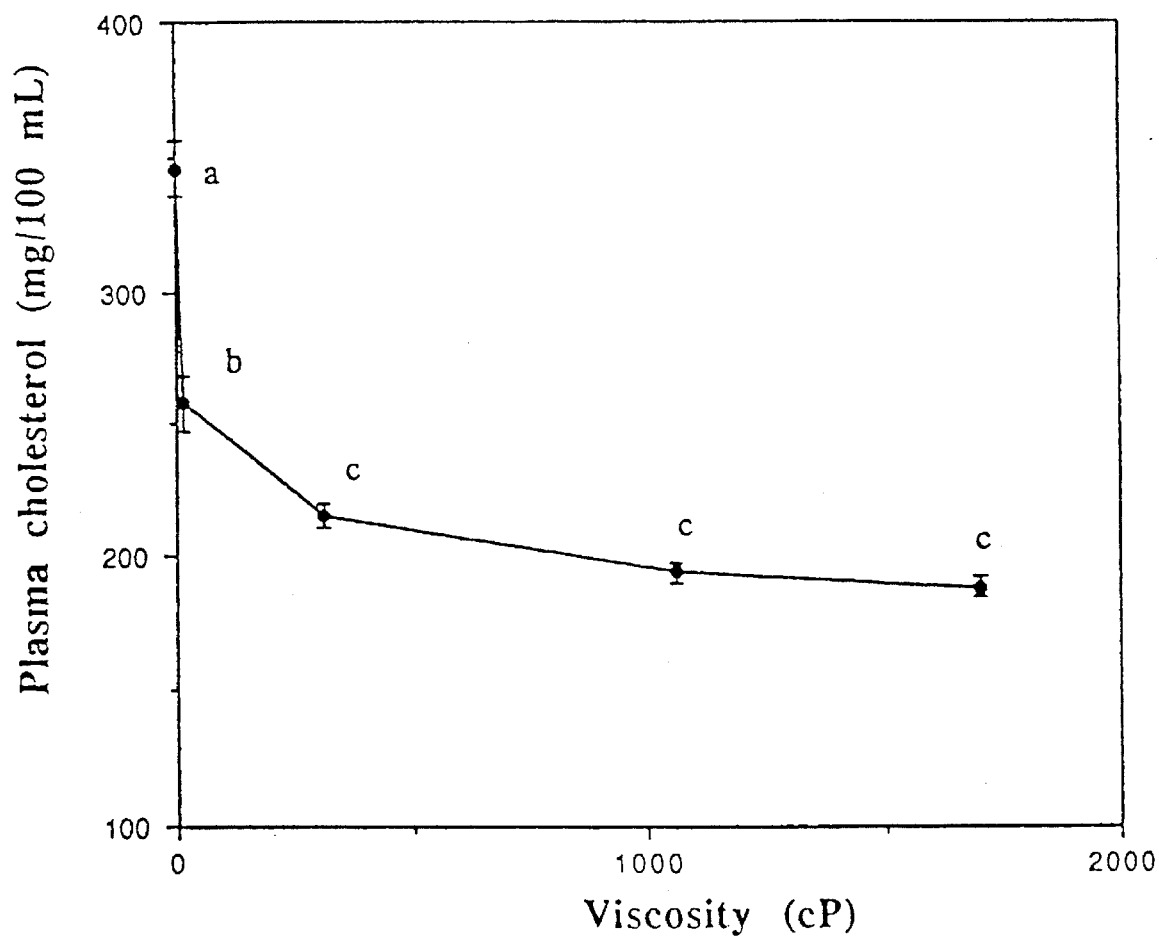
FIG. 1 is a plot of the relationship between in vitro viscosity of cellulose (a) and hydroxypropyl methyl-cellulose, and plasma total cholesterol in hamsters.

The cellulose ether compounds of the invention preferably contain lower alkyloxy (e,g,; $C_1$ to $C_4$) or hydroxy (lower(alkyloxy)) substituents, particularly, methoxyl and hydroxypropyloxyl groups. Cellulose ethers of this type, are described in U.S. Pat. Nos. 4,900,573, 4,734,285, 4,704,285, and in *Kirk-Othmer-Concise Encyclopedia of Chemical Technology*, M. Grayson, ed., Wiley-Interscience N.Y. (1985) at pages 231–232, the disclosures of which are incorporated herein by reference. Representative cellulose ethers used in the invention are methyl cellulose, 2-hydroxypropyl methyl cellulose, 2-hydroxyethyl methyl cellulose, 2-hydroxybutyl methyl cellulose, 2-hydroxyethyl ethyl cellulose, 2-hydroxypropyl cellulose, methyl ethyl cellulose, and 2-hydroxyethyl cellulose. High viscosity water soluble 2-hydroxypropyl methyl cellulose (HPMC) is particularly preferred.

The viscosities reported herein are measured in centipoises (cps or cP), as measured in a 1 or 2% by weight aqueous solution of the cellulose either at 20° C. using a rotational viscometer. The viscosity of 2% aqueous solutions of the cellulose ether employed in the invention is desirably in the range of 50–200,000 cps, and preferably in the range of 75–100,000 cps, most preferably within the range of 100–10,000 cps. A "high viscosity" cellulose ether possesses a viscosity of at least about 10,000 cps.

"Water soluble" for purposes of this application means that 2 grams of powdered cellulose ether can be dispersed by stirring into 100 grams of water at a temperature between 0° C.–100° C. to provide a substantially clear, stable aqueous composition or dispersion (when the dispersion is brought to 20° C.).

Cellulose ethers may be made by the reaction of cellulose pulp with various chemical reactants in the presence of caustic soda. For example, methylcellulose ether may be made by using chloromethane as the chemical reactant and HPMC may be made using propylene oxide and chloromethane as reactants. For example, see C. R. Noller, *Chemistry of Organic Compounds*, W. B. Saunders Co., London (2d ed. 1957) at pages 404–405.

The apparent viscosity of aqueous solutions of the cellulose ether compounds of this invention is proportional to the molecular weight or chain length of the compound. The number average molecular weight of water soluble high viscosity cellulose ethers useful in lowering the TPC levels in mammals is desirably at least about 100,000 daltons and preferably ranges from 100,000 to 250,000 daltons. The weight average molecular weight will be 3–10 times the number average molecular weight.

The cellulose ethers employed in this invention are further characterized in that they are non-toxic, non-ionic, noncaloric, biologically inert and edible.

The method for reducing the TPC level in the blood of mammals according to the present invention comprises administering an effective amount of a water soluble cellulose ether to the digestive tract of a mammal. One type of water soluble cellulose ether may be administered or a mixture of cellulose ethers may be administered. Preferably, the ether or ethers are administered in combination with a pharmaceutically-acceptable carrier, i.e., in one or more pharmaceutical unit dosage forms, such as tablets, gelatin capsules, pre-measured solutions intended for ingestion, and the like. While the method of administration may vary, the cellulose ethers are desirably administered orally and preferably are ingested by a human as an ingredient of his/her daily diet, i.e., in combination with a liquid vehicle, such as water, milk, vegetable oil, juice and the like, or in an ingestible solid or semi-solid matrix, such as in combination with conventional tabletting excipients, or in capsule fills such as polyethylene glycols, natural gels, and the like.

The cellulose ether can be administered directly (preferably in solution) or in powder form, or may be combined with other food ingredients. A number of foodstuffs which are generally compatible with cellulose ethers are disclosed by M. K. Weibel et al. (U.S. Pat. No. 4,923,981), the disclosure of which is incorporated by reference herein. For example, it may be mixed into foods such as shakes (i.e., milk shakes), breakfast drinks, juices and flavored drinks, yogurt, puddings, ice cream, ice milk, frozen yogurt, cheesecake filling, candy bars, including "health bars" such as granola and fruit bars, gums, hard candy, pastry fillings such as fruit fillings, cereals, breads, prepared stuffings and instant potatoes. Effective amounts of the present cellulose ethers can also be used as fat replacers in salad dressings, frosting, soups, sauces, gravies, mayonnaise and other spreads. Also, the cellulose ethers may be formulated as tablets, granules, capsules and the like. Therefore, "food ingredients," as the term is used herein, includes those ingredients commonly employed in recipes for the above foodstuffs, including flour, fruits, milk, eggs, starch, soy protein, sugar, sugar syrups, vegetable oils, butter, emulsifying agents such as lecithin, and the like.

Preferably, the water soluble cellulose ethers are partially or fully hydrated before they are orally ingested. For example, the cellulose ethers may be dispersed in sufficient water to make a syrupy liquid which then is mixed with one or more food ingredients such as flours and other cereal products to made a paste or dough, the latter being subsequently treated by such known food-preparing means as baking, extruding, and the like, to provide edible foodstuffs. Of course, colorings and flavorings may be added as may be appropriate to add to the attractiveness of the foodstuff. Food ingredients with which the cellulose ethers may be combined are metabolizable and have predetermined caloric values, and the amounts of such food ingredients that are used may be measured by their caloric content.

A functionally effective amount of the cellulose ether is employed. That amount is at least the minimum amount required to provide a significant reduction of the TPC levels in mammalian, e.g., human blood. Accordingly, the desired dosage or amount of water soluble cellulose ethers which should be included in the diet will vary depending on the size and sex of the human patient as well as the patient's TPC levels.

For example, the foodstuffs described above will typically be formulated to comprise from 2 to 20% of total cellulose ethers, depending on the viscosity grade of cellulose ether used and the type of foodstuff. Combinations of concentration and viscosity would have to be determined experimentally to some extent. For example, in a milk shake or pudding, the weight-% can be 10–20%. However, in baked goods, a range of only 2–5 wt-% might be possible, without deleteriously effecting the rheological characteristics of the product. Of course, the amount of cellulose ether incorporated into a pharmaceutical unit dosage form can be much higher, since taste and rheology are not primary considerations, e.g., from about 20–98%, preferably about 50–80% of cellulose ether can be used. Ingestion of from approximately 2 grams per 1,000 kilocalories (kcal) of total food consumed daily to approximately 30 grams per 1,000 kcal is appropriate in most circumstances. Preferably 10 to 20 grams per 1,000 kcal will be consumed daily.

The present invention is further described by the following non-limiting examples.

EXAMPLE 1

The ability of high and low viscosity preparations of HPMC to lower the total plasma cholesterol levels of hamsters was determined by comparing the total plasma cholesterol levels of animals fed diets which included the HPMC preparations compared to animals which were fed diets including high and low viscosity preparations of guar gum.

HPMC was obtained having a viscosity of approximately 100,000 cps for a 2% aqueous solution at 20° C. measured using a rotational viscometer. A Wells-Brookfield Viscometer model LVTD, cone and plate method was used as described in D. D. Gallaher et al., "The Effect Of Dietary Fiber Type On Glycated Hemoglobin And Renal Hypertrophy In The Adult Diabetic Rat", *Nutrition Research*, 10, 1311–1323 (1990), the teachings of which are herein incorporated by reference.

The high viscosity HPMC used in this Example was obtained from The Dow Chemical Company (METHOCEL™ K100LV Premium Grade, Lot #MM90041321K, sodium chloride content 0.6% by weight). The low viscosity HPMC had a viscosity of approximately 100 cps as a 2% aqueous solution at 20° measured using a Wells-Brookfield Viscometer as described above.

Guar gum is commercially available and is naturally viscous. The high viscosity guar gum used in this Example was obtained from the Sigma Chemical Company and had a 2% by weight aqueous solution viscosity of approximately 100,000 cps at 20° C., determined as described above.

The low viscosity guar gum used in this invention was obtained from The Dow Chemical Company. Its viscosity (as a 2% by weight aqueous solution at 20° C.) was about 64 cps at a shear rate of 6 reciprocal seconds, using an A Wells-Brookfield Viscometer model LVTD. The low viscosity guar gum was prepared by reducing the viscosity of the natural guar gum by limited acid hydrolysis according to well known acid hydrolysis techniques.

Each of the high and low viscosity preparations of. HPMC and of guar gum were blended with the various other ingredients of the animal's diet described below in a Hobart A-120 vertical mixer. The diet containing the above-described preparations was fed to four sets each containing 16 male Golden Syrian hamsters for a six-week period. The hamsters ranged in weight from 79 to 121 grams.

The diet used contained the ingredients listed on Table 1, below:

TABLE 1

| INGREDIENT | AMOUNT OF g/kg/DIET |
|---|---|
| Casein, 85% protein, commercially obtained | 200 |
| DL-Methionine | 3 |
| Cornstarch | 497.8 |
| Sucrose | 100 |
| HPMC or Guar Gum | 50 |
| Plam oil | 100 |
| AIN Mineral Mix[1] | 35 |
| AIN Vitamin Mix[2] | 10 |
| Choline bitartrate | 2 |
| Vitamin K | 1.33 (mg) |
| BHT | 1 |
| Cholesterol | 1.2 |

[1]Percent of mineral mix: $CaHPO_4$, 50.0; NaCl, 7.4; K citrate.$H_2O$, 22.0; $K_2SO_4$, 5.2; MgO, 2.4; manganous $CO_3$, 0.35; ferric citrate, 0.60; $ZnCO_3$, 0.16; $CuCO_3$, 0.03; $KIO_3$, 0.001; $Na_2SeO_3$.$5H_2O$, 0.001; $CrK(SO_4)_2$.$12H_2O$, 0.055; sucrose, powdered, 11.8.
The total dietary calcium and phosphorous, respectively, with various protein sources will be approximately (mg per 100 g of diet): crude casein, 656 and 620; purified casein, 520 and 560; isolated soy protein, 558 and 552.
[2]Per kg of vitamin mixture (g); thiamin HCl, 0.6; riboflavin, 0.6; pyridoxine HCl, 0.7; niacin, 3.0; Ca pantothenate, 1.6; folic acid, 0.2; biotin, 0.020; vitamin $B_{12}$, 1 mg; vitamin A, 400,000 IU; vitamin E, 5,000 IU; vitamin $D_3$, 2.5 mg; vitamin K, 5.0 mg; sucrose, powdered, to make 1,000 g.

Each hamster ingested approximately 8 g of the feed each day. After six weeks, the hamsters were sacrificed to obtain plasma samples. The TPC levels were measured enzymatically using a modification of the method of C. A. Allain et al, "Enzymatic Determination of Total Serum Cholesterol," *Chin. Chem.*, 20, 470 (1974), the teachings of which are incorporated herein by reference. Briefly, cholesterol esters in the sample were hydrolyzed by cholesterol esterase to cholesterol which was then oxidized by cholesterol oxidase to cholest-4-en-3-one and hydrogen peroxide. The latter was then coupled with the chromogen, 4-aminobenzenesulfonate in the presence of peroxidase to yield a quinoneimine dye which has an absorbance maximum of 500 nm. The intensity of the color that is produced is directly proportional to the total cholesterol concentration in the sample.

The amounts of free cholesterol ester in the liver was calculated as follows. A 1 g portion of-each liver was obtained and combined with a chloroform:methanol solvent (2:1) to extract the lipids using well known lipid extraction techniques. The mixture was filtered, aliquots of filtrate were taken to dryness, brought up in a non-ionic detergent, dried and then the cholesterol levels were determined enzymatically.

To determine the level of free cholesterol level in a sample the enzyme assay described above was modified according to the method described in *Clin. Chem.*, 28, 1379 (1982), to leave out the step of combining the sample with esterase. The rest of the procedure was unchanged. The intensity of color that is produced is directly proportional to the free cholesterol concentration in the sample.

In order to determine the level of cholesterol ester, the total cholesterol level of the liver sample was determined according to the method described above. The concentration of cholesterol ester present in the sample was determined by subtracting the free cholesterol concentration from the total cholesterol concentration.

The results are shown below on Table 2.

TABLE 2

| Diet | Plasma (mg/dl) | Liver (mg/g wet wt) | |
|---|---|---|---|
| (n = 16) | C | Free C | C Ester |
| LG | 214.5 ± 10.2$^a$ | 2.8 ± 0.2$^{ab}$ | 20.2 ± 2.2$^a$ |
| LM | 223.3 ± 11.7$^a$ | 3.2 ± 0.3$^{ab}$ | 20.2 ± 1.8$^a$ |
| HG | 170.1 ± 7.8$^b$ | 2.4 ± 0.1$^b$ | 13.2 ± 1.4$^b$ |
| HM | 151.9 ± 7.9$^b$ | 2.4 ± 0.1$^b$ | 4.8 ± 0.6$^c$ |

Values are mean ± SEM. Values in a column with different superscripts are different ($P < 0.05$).
LG — Low viscosity guar gum
LM — Low viscosity HPMC
HG — High viscosity guar gum
HM — High viscosity HPMC Total plasma cholesterol was statistically significantly lower in the high viscosity guar gum and high viscosity HPMC groups compared to the low viscosity guar gum and low viscosity HPMC groups. Liver cholesterol esters were lowest in the high viscosity HM group, followed by the high viscosity guar gum group. Similarly, free cholesterol in the liver was lower in animals which ingested the high viscosity compounds.

EXAMPLE 2

Effect of HPMC of Varying Viscosity Grades

Male golden Syrian Hamsters (Harlan Sprague Dawley Inc., Indianapolis, Ind.), initially weighing 80–100 g were housed individually in stainless steel mesh cages and were fed a commercial rat ration (Rodent Laboratory Chow 5001, Purina Laboratories) and water ad libitum for 3 days to allow adaptation to the environment. The purified experimental diet was prepared according to Example 1, except that cellulose and four different viscosity grades of hydroxypropyl methylcellulose (HPMC) (Type K METHOCEL®, Dow, U.S.A., Midland, Mich.) (19–24% methoxy; 4–12% hydroxypropoxy) were used as dietary fiber sources. HPMC formulations were mixed in the diet as follows: extremely high viscosity (EV) HPMC was K100M (100,000 cps viscosity), high viscosity (HV) HPMC was made from a mixture of 60% (w/w) of K100M and 40% of K15M (15,000 cps viscosity), moderate viscosity (MV) HPMC was made by a mixture of 65% (w/w) of K15M and 35% of K4M (4,000 cps viscosity), and low viscosity (LV) HPMC was K100 LV (100 cps viscosity). Commercial designations of METHOCEL® products are based on viscosity values (±20%) determined in water at 20° C. with a concentration of 2% METHOCEL®. The viscosities were measured again at 1% solution in water at 37° C. (see below). In the experimental protocol, hamsters were randomly divided into 5 treatment groups; food intake and body weight were estimated weekly.

Food intake was corrected for spillage.

After 3 weeks of ad libitum feeding, intestinal contents viscosity and total plasma cholesterol concentration were measured. Apparent viscosity measurements were based on the ASTM monograph D1347 and D2363 (DOW U.S.A.). Heated water (80°–90° C.) was added to HPMC powder to make a 1% solution. The solution was stirred for 10 minutes and placed in an ice bath, stirred, and allowed to remain in the ice bath for 40 minutes to ensure that hydration and solution were complete. The solution was centrifuged to expel any entrapped air. The temperature of the solution was adjusted to 37° C. and the viscosity was measured at several shear rates by using a Wells-Brookfield cone/plate viscometer (Brookfield Engineering, Stoughton, Mass.). Aqueous solutions of HPMC exhibit pseudoplastic flow behavior where apparent viscosity decreases with increasing rate of shear. The plot of shear rate versus viscosity on log-log paper was almost a straight line, and therefore could be used for prediction of viscosity at a certain shear rate. For purposes of comparison, values were obtained for a fixed rate of shear by extrapolation.

After 3 weeks of feeding the diets, hamsters were anesthetized with ether and blood was collected by cardiac puncture in tubes containing ethylenediamine tetraacetic acid (EDTA) (1 mg/ml blood) for total plasma cholesterol analysis (Sigma Diagnostics, St. Louis, Mo.). The small intestine and cecum were removed and the cecum weighed. The small intestine was stripped carefully to collect the contents; the contents were centrifuged at 30,000×g in a J2-21 high speed centrifuge using a JA 20.1 rotor (Beckman Instruments, Spinco Div, Palo Alto, Calif.) for 30 min at 4° C. The volume of supernatant was recorded and the viscosity of the supernatant (presumed to be a non-Newtonian liquid) was measured as described above. Viscosity was expressed as centipoise (cP). Values were analyzed by one-way analysis of variance. Differences among means were inspected using Ducan's multiple-range test. Means were considered to be significant at $p<0.05$.

The apparent viscosities of the aqueous solutions (1%) of cellulose and of HPMC are shown in Table 3.

TABLE 3

Apparent (in vitro) viscosity of dietary additives and ex-vivo viscosity of intestinal contents of hamsters fed the experimental diets.

| Dietary Additive | Viscosity (cP) Additive (1% soln) | (2% soln) | Intestinal contents |
|---|---|---|---|
| Cellulose | 1 | 10 | $2 \pm 0.3^c$ |
| LV[a] | 14 | 100 | $47 \pm 9.5^{bc}$ |
| MV[b] | 305 | $10^3$ | $111 \pm 21.9^{bc}$ |
| HV[c] | 1059 | $10^4$ | $257 \pm 122.8^b$ |
| EV[d] | 1698 | $10^5$ | $557 \pm 127.5^a$ |

[a]LV = low viscosity hydroxypropyl methylcellulose (HPMC),
[b]MV = medium viscosity HPMC,
[c]HV = high viscosity HPMC, and
[d]EV = extremely high viscosity HPMC. Viscosities of 1% aqueous solution of HPMC are manufacturer's values. In vitro viscosity of cellulose is arbitrary. Values of the intestinal contents viscosity (ex-vivo) represent means ± SEM of 10–12 samples (a few were pooled). Means in the last column with different superscript letters are significantly different at $p < 0.05$.

There was found to be a positive linear relationship between in vitro and ex-vivo viscosity ($r^2=0.952$) of HPMC. This suggests that, under the conditions of this experiment, ex-vivo viscosities may be predicted from in vitro viscosities.

HPMC is a carbohydrate polymer which dissolves in water by swelling and subsequent hydration. As expected, the liquid volume of intestinal contents was increased with increasing ex-vivo viscosity. Liquid volume seems to reach a plateau after about 250 cP of ex-vivo viscosity. The weight of the cecum as determined with its contents tended to be heavier in hamsters fed high viscosity HPMC.

Figure 2:
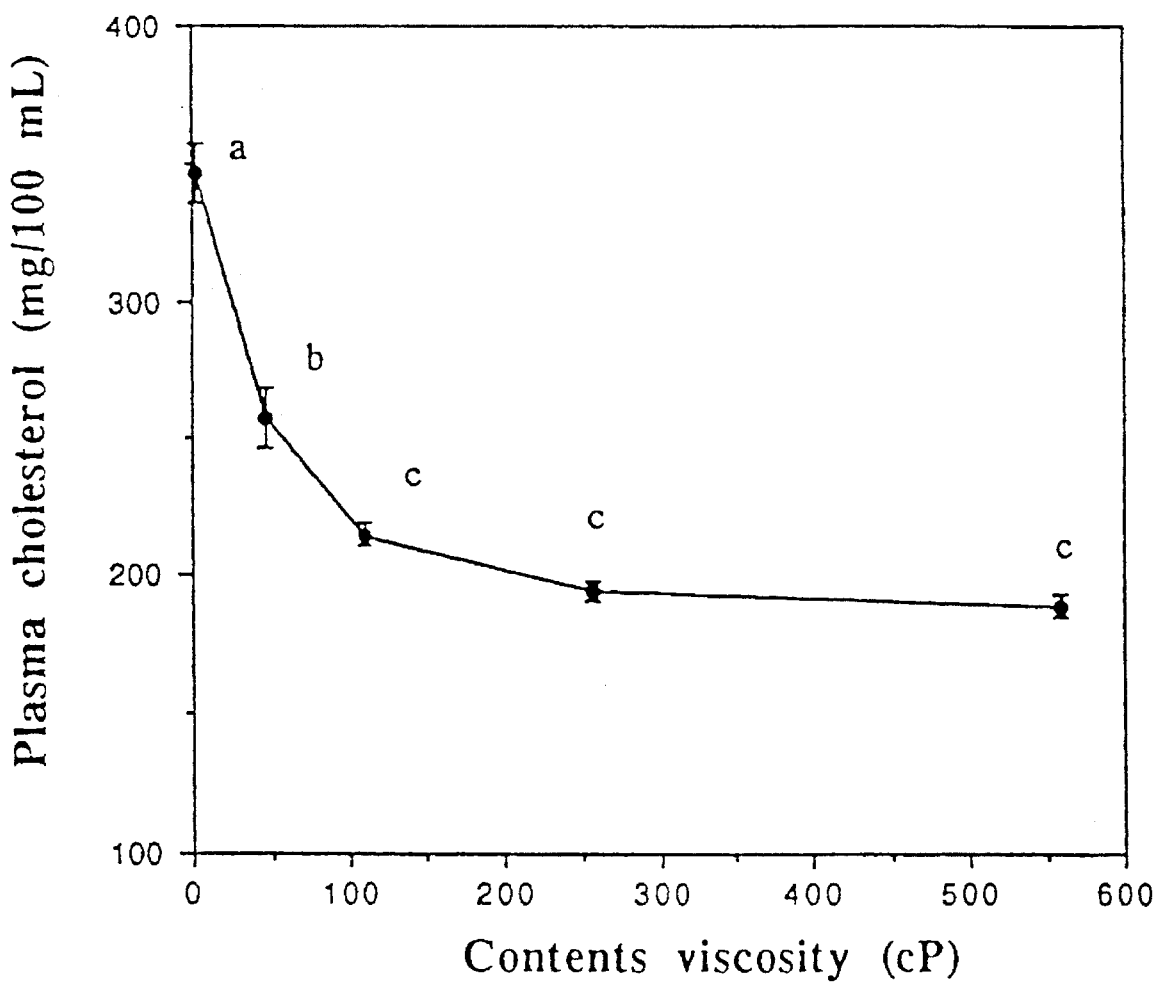
FIG. 2 is a plot of the relationship between the ex-vivo contents viscosity of cellulose (a) and HPMC, and plasma total cholesterol in hamsters.

The effect of in vitro and ex-vivo viscosity of cellulose and HPMC on total plasma cholesterol is shown in FIGS. 1 and 2, respectively, wherein each point in FIG. 1 represents the in vitro viscosity (cP=centipoise) of the 1% cellulose or HPMC solutions shown in Table 3 and plasma total cholesterol concentration (mg/100 ml) after feeding the diets for 3 weeks. Each plasma total cholesterol concentration value represents mean ±SEM of 12–13 animals. Means of the plasma cholesterol not sharing a common superscript are significantly different ($p<0.05$).

Each point in FIG. 2 represents the viscosity (exvivo) of intestinal content and plasma total cholesterol concentration (mg/dl) after feeding the diet for 3 weeks. Each plasma total cholesterol concentration value and exvivo viscosity value represents mean ±SEM of 12–13 animals and 10 to 12 animals, respectively. Values of the plasma cholesterol not sharing a common superscript are significantly different ($p<0.05$).

The two figures show a very similar relationship due to the high correlation between in vitro and ex-vivo viscosity. This finding suggests that, under these conditions, in vitro viscosities may be useful to predict the cholesterol lowering capability of a cellulose ether. The total plasma cholesterol of all HPMC treatments was markedly lower compared to cellulose control (point superscript a in each figure).

Although the total plasma cholesterol-lowering effect appeared to be somewhat greater in HPMC with higher viscosity, the difference was statistically significant only between LV and MV HPMC. Total plasma cholesterol was reduced dramatically as ex-vivo viscosities of the 1% solutions increased to about 150 cP. Further increases in ex-vivo viscosities produced no additional hypocholesterolemic response.

When these data are plotted on a logarithmic scale, there is a highly linear relationship between plasma cholesterol and ex-vivo viscosity ($r^2=0.982$) (data not shown).

All patents, patent applications and publications cited hereinabove, are incorporated by reference herein. While a preferred embodiment of the present invention has been described, it should be understood that various changes, adaptations and modifications may be made therein without departing from the spirit of the invention and the scope of the appended claims.

What is claimed is:

1. A nutritious foodstuff capable of reducing total plasma cholesterol levels in mammals, consisting essentially of a mixture of about 2–20 weight percent of hydroxypropyl methyl cellulose having a viscosity, measured as a 2 weight percent aqueous solution of 20° C., of about 50–4,000 cps, and at least one separate metabolizable food ingredient having a predetermined caloric content.

2. The foodstuff of claim 1 wherein the foodstuff includes sufficient water to moisten and expand the hydroxypropyl methyl cellulose.

3. A nutritious foodstuff capable of reducing total plasma cholesterol levels in mammals, consisting essentially of a mixture of about 2–15 weight percent of hydroxypropyl methyl cellulose formed by combining a powdered, water-soluble, hydroxypropyl methyl cellulose having a viscosity, measured as a 2 weight percent aqueous solution at 20° C., of about 50–4,000 cps, with sufficient water to cause the hydroxypropyl methyl cellulose to expand, and at least one separate metabolizable food ingredient having a predetermined caloric content, so that ingestion of the foodstuff provides from 2 to 10 grams of said cellulose per each 1,000 kcal of total food consumed daily.

* * * * *